United States Patent [19]

Besecke et al.

[11] 4,228,102
[45] Oct. 14, 1980

[54] PREPARATION OF CARBOXYLIC ACID AMIDES

[75] Inventors: Siegmund Besecke, Darmstadt; Wolfgang Gaenzler, Darmstadt-Arheilgen; Guenter Schroeder, Ober-Ramstadt, all of Fed. Rep. of Germany

[73] Assignee: Röhm GmbH, Darmstadt, Fed. Rep. of Germany

[21] Appl. No.: 14,361

[22] Filed: Feb. 23, 1979

[30] Foreign Application Priority Data

Mar. 3, 1978 [DE] Fed. Rep. of Germany ....... 2809102

[51] Int. Cl.$^3$ .......................................... C07C 102/06
[52] U.S. Cl. ........................ 260/561 N; 260/507 R; 260/513 N; 260/556 A; 260/556 B; 260/558 A; 260/559 A; 260/561 A; 260/558 R; 260/559 R; 260/561 R; 260/562 R; 560/43; 560/172; 562/433; 562/455; 562/574
[58] Field of Search ........... 260/561 N, 562 R, 507 R, 260/513 N, 556 A, 556 B, 558 A, 559 A, 561 A, 558 R, 559 R, 561 R; 560/43, 172; 562/433, 574, 455

[56] References Cited

U.S. PATENT DOCUMENTS

| | | | |
|---|---|---|---|
| 2,451,436 | 12/1948 | Erickson | 260/561 A |
| 2,529,838 | 11/1950 | Erickson | 260/561 N |
| 2,683,741 | 7/1954 | Wiley | 260/561 N |
| 2,719,175 | 9/1955 | Coover et al. | 260/562 R |
| 3,878,247 | 4/1975 | Moss et al. | 260/561 N |
| 3,945,970 | 3/1976 | Spoerke | 260/562 R |

FOREIGN PATENT DOCUMENTS

752481  1/1945 Fed. Rep. of Germany .

OTHER PUBLICATIONS

Arcus, J. Chem. Soc. 1949, pp. 2735–2740.

Weisel, J. Am. Chem. Soc. 1945 (67), pp. 1071–1072.

*Primary Examiner*—Arthur P. Demers
*Attorney, Agent, or Firm*—Curtis, Morris & Safford

[57] ABSTRACT

What is disclosed is a method for making amides of the formula

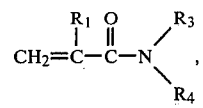

wherein
$R_1$ is hydrogen or methyl,
$R_3$ is straight-chain or branched alkyl or unsubstituted or substituted aryl, and
$R_4$ is hydrogen or straight-chain or branched unsubstituted or substituted alkyl, which comprises reacting an ester of the formula

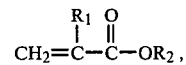

wherein $R_2$ is alkyl having 1 to 6 carbon atoms, with heating and under autogenous pressure, in a homogeneous phase, with an amine of the formula

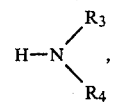

said amine being present in an amount which is stoichiometrically deficient up to an amount which is in small stoichiometric excess with respect to said ester.

10 Claims, No Drawings

PREPARATION OF CARBOXYLIC ACID AMIDES

The present invention relates to a method for making certain α,β-ethylenically unsaturated carboxylic acid amines.

Amides of α,β-ethylenically unsaturated carboxylic acids, particularly of acrylic acid and methacrylic acid, are of industrial interest as polymerizable monomers having a relatively hydrophilic, inert functional group.

When selecting a suitable method of production, the question of the availability of the starting compound or compounds involved is of decisive importance among the technical aspects.

As is known, esters of α,β-unsaturated carboxylic acids, particularly the esters of acrylic acid and methacrylic acid, are the monomeric building blocks of valuable industrial polymers. At first sight, the aminolysis of the corresponding esters of the said unsaturated carboxylic acids would appear to offer itself as the method of choice for the production of the acid amides, in which case, to be sure, the two reactive centers present in the molecule can react competitively.

A paper from the year 1949 reports on the reaction of methyl methacrylate with concentrated ammonia (7 days at room temperature) with the formation of methacrylic acid amide (C. L. Arcus, J. Chem. Soc. 1949, 2732). However, this reaction cannot be carried out with alkyl amines or dialkyl amines. From earlier studies by Weisel et al. on the reaction of ethylmethacrylate with piperidine, it was known that, primarily, an addition reaction leading to β-piperidinoisobutyrate takes place [Weisel et al., J. Am. Chem. Soc. 67, 1071 (1945)]. In fact, in the reaction of methyl acrylate or methylmethacrylate with a 2-fold to 4-fold excess of primary or secondary amines (but only insofar as higher boiling amines are concerned) for about 6 to 10 hours at about 100° C. to 180° C., the β-N-(di)alkyl-amino-N:(di)alkyl isobutyric-acid amides or propionic-acid amides are obtained as the primary product (German published patent application DE-AS 2,502,247).

In principle, the possibility of thermally eliminating amino groups in the β-position to an acid amide group, with the formation of a double bond, is to be sure known in the art.

However, if the prior art methods are applied to the present problem, namely the production of the corresponding acryl- or methacryl-N-(di)alkylamides from the β-(dialkylamino)-N-(di)-alkyl-propionic-acid amides or -isobutyric-acid amides, immense difficulties are encountered.

Under the usual conditions, i.e., with heat treatment at 200° C. and 300° C., both the conversion itself as well as the purity of the resultant products are entirely unsatisfactory. In addition, there is a pronounced tendency of the (desired) α,β-unsaturated amides to react further, for instance with polymerization, or to dimerize by addition of amide to the double bond.

Furthermore, such a method is limited by its very nature to amides of higher boiling amines (see above).

It has now been found that it is possible, surprisingly, to make an amide of the formula

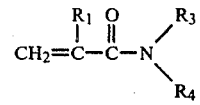

by reacting an α,β-unsaturated ester of the formula

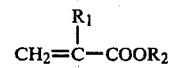

with an amine of the formula

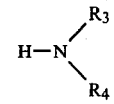

in a single step reaction with the formation of an alcohol of the formula $R_2OH$ if the ester and amine are reacted in a homogeneous phase with heating and under autogenous pressure, the amine being present in an amount which can be stoichiometrically deficient up to a slight stoichiometric excess with respect to the ester. In the formulas, $R_1$ is hydrogen or methyl, $R_2$ is alkyl having 1 to 6 carbon atoms, preferably 1 to 3 carbon atoms, $R_3$ is straight-chain or branched alkyl having 1 to 18 carbon atoms, preferably 1 to 4 carbon atoms, or is aryl such as phenyl or naphthyl, wherein said alkyl or aryl may be substituted, and $R_4$ is hydrogen or straight-chain or branched alkyl having 1 to 18 carbon atoms, preferably 1 to 4 carbon atoms, wherein said alkyl may be substituted.

As substituents for $R_3$ and $R_4$, mention may be made, in particular, of carboxy, alkoxycarbonyl, (alkyl)carbamoyl, sulfo, sulfoamido, and particularly (alkyl) amino groups. If the substituents bear one or two alkyl groups, groups having 1 to 6 carbon atoms are preferred.

Accordingly, the amines can be represented by the formula

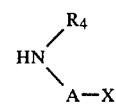

wherein $R_4$ has the meaning given earlier, A is $-(CR_5R_6)_n$, phenylene, or naphthylene, $R_5$ is hydrogen or alkyl having 1 to 6 carbon atoms or is phenyl, $R_6$ is hydrogen or alkyl having 1 to 6 carbon atoms, X is hydrogen or a $-COOH$, $-CONR_7R_8$, $-COOR_9$, $-SO_3H$, $-SO_2NR_7R_8$ or $-NR_7'R_8'$ group, and n is a whole number from 1 to 18. However, n can only be one if X is not $-NR_7'R_8'$. $R_7$ and $R_8$, as well as $R_7'$ and $R_8'$, independently of each other represent hydrogen or alkyl having 1 to 6 carbon atoms. $R_9$ represents alkyl having 1 to 6 carbon atoms.

$R_5$ and/or $R_6$ (insofar as they represent alkyl) predominantly stand only once per molecule for an alkyl radical having 1 to 6 carbon atoms and otherwise for hydrogen. When n is greater than 1 there thus can be $-CR_5R_6-$ alkylene radicals which differ from each other.

The amine compounds of

thus comprise, for instance, amimo acids and their esters and amides, such as glycine and alanine, as well as alkylenediamines such as ethylene diamine, propylene diamine, hexamethylene diamine, phenylene diamine, neopentane diamine, and dimethylaminoneopentanamine, as well as sarcosine. If, within the scope of the present invention, amine compounds are used which contain a second primary or secondary amino group, for instance alkylenediamines, then a reaction thereof with two molecules of the $\alpha,\beta$-unsaturated ester is possible. This type of reaction to form a bis-amido compound is also included in the protection sought.

The method of the invention preferably proceeds using an ester compound in which $R_1$ and $R_2$ stand for methyl (i.e. from methyl methacrylate). It should be emphasized in particular that the reaction of the $\alpha,\beta$-unsaturated esters according to the present invention leads to amides, even if the amine is used in a stoichiometrically deficient amount.

The ratio of the ester compound to the amine can be from about 1:0.1 to about 1:1.5, but the use of an excess of amine is rather to be considered an exception.

It can be considered a particularly surprising aspect of the method of the invention that the reaction takes place very readily even with relatively low molecular weight and low-boiling amines, such as methylamine, ethylamine, n-propylamine, and isopropylamine, particularly when $R_1$ and $R_2$ are methyl. The embodiment of the method of the invention in which $R_3$ is alkyl having 1 to 4 carbon atoms and $R_4$ is hydrogen is particularly preferred.

The reaction of the invention is generally carried out at a temperature above 150° C., preferably between 180° C. and 250° C., in a homogeneous phase. The pressure contemplated in accordance with the process is, as a rule, of an autogenous nature and is thus dependent on the nature of the reactants. It lies approximately within the range from atmospheric pressure up to about 20 atmospheres, but pressures above 20 atmospheres are also compatible with the reaction.

The presence of slight, preferably catalytic, concentrations of protons, preferably in the form of HCl, serves to favor the reaction. For example, the reaction in accordance with the invention is advantageously carried out in the presence of 0.01 to 0.1 mol of HCl, referred to 1 mol of the amine reactant used, preferably with an acid addition salt of the amine.

The reaction of the invention is advantageously carried out under conditions in which side reactions are avoided and in the presence of stabilizing agents. The influence of iron has proven particularly favorable as a stabilizer, whether iron, preferably in the form of ferric compounds, is added to the batch or whether iron is used as part of the apparatus employed, for instance in the form of column packing bodies. Because of the oxidative action of atmospheric oxygen, iron present or added as elemental iron or as ferrous ion is probably ultimately present in the system as ferric ion. The addition of copper compounds, hydroquinone, and other stabilizers has also proved satisfactory. It must be considered particularly surprising that on the basis of the experience at hand, for instance with methyl methacrylate as the starting compound of formula II, it is unnecessary continuously to remove the alcohol which is formed—methanol in this specific case.

The yields of amides according to the method of the invention are surprisingly high. The amide product obtained according to the invention is furthermore characterized by its purity, as compared with products obtainable by the prior art methods described.

A better understanding of the present invention and of its many advantages will be had by referring to the following specific examples, given by way of illustration.

EXAMPLE 1

300 g (3 mols) of methyl methacrylate, 96.1 g (3.3 mols) of monomethylamine, and 6.75 g (0.1 mol) of monomethylamine hydrochloride were heated in the presence of 4 g of ferric acetylacetonate and 50 ppm of hydroquinone for 2½ hours at 190° C. in a steel autoclave. The pressure passed through a maximum value of 16 atmospheres.

With 97% conversion of methyl methacrylate, 240 g of N-methylmethacrylic acid amide were obtained (corresponding to 81% yield, referred to the methyl methacrylate employed).

After fractional vacuum distillation over a column packed with iron bodies, 221 g of pure product were isolated (corresponding to 71% of the theoretical value, referred to the methyl methacrylate used).

EXAMPLE 2

500 g (5 mols) of methyl methacrylate, 325 g (5.5 mols) of isopropylamine, and 12.4 g (0.13 mol) of isopropylamine hydrochloride were reacted in the presence of 0.03 mol of ferric acetylacetonate for 2½ hours in a steel autoclave at 220° C. The pressure increased to a maximum of 18 atmospheres. The methyl methacrylate reacted to the extent of 80% and gave 442 g of N-isopropylmethacrylic acid amide (corresponding to a 68% yield referred to the methyl methacrylate used).

EXAMPLE 3 (Comparison Example)

100 g (1 mol) of methyl methacrylate and 65 g (1.1 mols) of isopropylamine were stirred for 120 hours at room temperature in the presence of 2.5 g (0.03 mol) of isopropylamine hydrochloride and 0.006 mol of ferric acetylacetonate. As the sole product, there was obtained, with a selectivity of 100%, 37 g of $\beta$-(N-isopropylamine)-iso-butyric acid methylester (corresponding to a 23% yield, referred to the methyl methacrylate used).

EXAMPLE 4

300 g (3 mols) of methyl methacrylate and 135 g (3 mols) of dimethylamine reacted to the extent of 75% in the presence of 0.3 mol of dimethylamine hydrochloride and 1 g of copper oleate, within 2 hours at 190° C. ($p_{max}=11$ atmospheres) in a steel autoclave. There were formed thereby 46 g (=about 18%) of N,N-dimethyl-methacrylic acid amide, 78 g (=about 22%) of $\beta$-(N,N-dimethylamine)-N',N'-dimethyl-isobutyric acid amide, and 196 g (=about 60%) of $\beta$-(N,N'-dimethylamine)-isobutyric acid methylester.

EXAMPLES 5 AND 6

200 g (2 mols) of methyl methacrylate reacted with 31.06 g (1 mol) and 15.53 g (0.5 mol) of methylamine, respectively, in the presence of 3.4 g (0.05 mol) of methylamine hydrochloride within 2½ hours at 190° C. with yields of 88% and 56%, respectively (referred to the amine used). N-methyl methacrylic acid amide was produced thereby with a selectivity of 89% and 97%, respectively.

EXAMPLE 7

344 g (4 mols) of methyl acrylate were reacted with 236 g (4 mols) of isopropylamine in the presence of 100 ppm of hydroquinone, 5.8 g of ferric acetylacetonate, and 9.6 g (0.1 mol) of isopropylamine hydrochloride for 2½ hours at 200° C. in a steel autoclave with 90% conversion ($p_{max}=9$ atmospheres).

There were produced thereby 196 g of N-isopropylacrylic acid amide (corresponding to a 58% yield, referred to the methylacrylate used).

EXAMPLE 8

Example 1 was repeated, but ferric acetylacetonate was replaced as stabilizer by 1 g of copper oleate.

With a 98% conversion of methyl methacrylate, 246 g of N-methylmethacrylic acid amide were obtained (corresponding to an 83% yield referred to the methyl methacrylate used).

EXAMPLE 9

426 g (3 mols) of butyl methacrylate, 390 g (3 mols) of N,N,2,2-tetramethylpropane-1,3-diamine, 29.4 g (0.3 mol) of $H_3PO_4$, and 2 g of hydroquinone were warmed for 2 hours at 220° C. N-(3-dimethylamino-2,2-dimethylpropyl)-methacrylic acid amide was formed in this way. Yield: 60% (selectivity: 94% calculated on the reacted butyl methacrylate).

EXAMPLE 10

1.9 mols of α-naphthylamine, 4 mols of methyl methacrylate, 1 percent by weight of iron-(III)-acetylacetonate, 0.1 mol of HCl, and 100 ppm of hydroquinone were heated in a 2-liter V4A-stainless steel stirred autoclave for 3 hours at 250° C. In this way, methacrylic acid naphthalide formed (yield: 15%). Selectivity, calculated on the amount of methyl methacrylate reacted, was greater than 90%.

Similar results are obtained in the reaction of methyl methacrylate with aniline.

EXAMPLE 11

200 g of methyl methacrylate, 129 g of dibutylamine, 8.25 g of dibutylamine hydrochloride, 5 g of Fe-(III)-acetylacetonate, and 0.5 g of hydroquinone were heated for 3 hours at 230° C. in an autoclave ($p_{max}=10$ atmospheres). In this way, a 15% yield of N,N-dibutylmethacrylic acid amide form. The selectivity, calculated on the methyl methacrylate reacted, was greater than 80%.

EXAMPLE 12

200 g of methyl methacrylate and 142 g of isopropylamine were heated at 190° C. for 2½ hours in a 0.5-liter stirred autoclave ($p_{max}=15$ atmospheres). N-isopropylmethacrylic acid amide was formed in this way in a 32% yield.

If the same reaction is carried out in the presence of 2 g of HCl, N-isopropylmethacrylic acid amide is obtained in a 51% yield. Selectivity: greater than 90%.

What is claimed is:

1. A method for making an amide of the formula

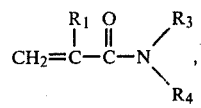

wherein $R_1$ is hydrogen or methyl, $R_4$ is hydrogen, straight-chain or branched alkyl, or straight-chain or branched alkyl substituted by carboxy, alkoxycarbonyl, (alkyl)carbamoyl, sulfo, sulfoamido, or (alkyl)amino, and $R_3$ is $-AX$, wherein A is $-(CR_5R_6)_n$, phenylene, or naphthalene, $R_5$ is hydrogen or alkyl having 1 to 6 carbon atoms, $R_6$ is hydroxy or alkyl having 1 to 6 carbon atoms, X is hydrogen, carboxy, alkoxycarbonyl, (alkyl)carbamoyl, sulfo, sulfoamido, or (alkyl)amino and n is a whole number from 1 to 18 if X is other than (alkyl)amino or is a whole number from 2 to 18 if X is alkylamino, which method comprises reacting an ester of the formula

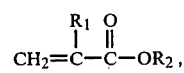

wherein $R_2$ is alkyl having 1 to 6 carbon atoms, with heating and under pressure, in a homogeneous phase in the presence of a catalytic concentration of protons, with an amine of the formula

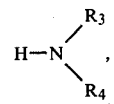

said amine being present in an amount which is stoichiometrically deficient up to an amount which is in small stoichiometric excess with respect to said ester.

2. A method as in claim 1 wherein the ester and amine are reacted at a temperature above about 150° C.

3. A method as in claim 2 wherein said temperature is between about 180° C. and about 250° C.

4. A method as in claim 1 wherein said protons are present as HCl.

5. A method as in claim 1 wherein the reaction is carried out in the additional presence of a stabilizer selected from the group consisting of iron, copper, and hydroquinone.

6. A method as in claim 4 wherein said stabilizer is iron.

7. A method as in claim 4 wherein said iron is present as a ferric compound.

8. A method as in claim 1 wherein $R_4$ is hydrogen or straight-chain or branched alkyl and $R_3$ is $-AX$ wherein X is hydrogen.

9. A method as in claim 1 wherein $R_4$ is hydrogen or straight-chain or branched alkyl having 1 to 18 carbon atoms and $R_4$ is straight-chain or branched alkyl having 1 to 18 carbon atoms, phenyl, or naphthyl.

10. A method as in claim 1 wherein $R_4$ is hydrogen and $R_3$ is alkyl having 1 to 4 carbon atoms.

* * * * *